US008291900B2

(12) United States Patent
Quoniam

(10) Patent No.: US 8,291,900 B2
(45) Date of Patent: Oct. 23, 2012

(54) BLISTER ASSEMBLY FOR INHALATION DEVICE

(75) Inventor: Michel Quoniam, La Madeleine de Nonancourt (FR)

(73) Assignee: Aptar France SAS, Le Neubourg (FR)

( * ) Notice: Subject to any disclaimer, the term of this patent is extended or adjusted under 35 U.S.C. 154(b) by 800 days.

(21) Appl. No.: 11/631,955

(22) PCT Filed: Jul. 11, 2005

(86) PCT No.: PCT/EP2005/053313
§ 371 (c)(1),
(2), (4) Date: Jan. 9, 2007

(87) PCT Pub. No.: WO2006/010704
PCT Pub. Date: Feb. 2, 2006

(65) Prior Publication Data
US 2008/0072898 A1  Mar. 27, 2008

(30) Foreign Application Priority Data

Jul. 9, 2004  (FR) ...................... 04 51480

(51) Int. Cl.
*A61M 15/00* (2006.01)
*A61M 13/00* (2006.01)
*B65D 83/06* (2006.01)

(52) U.S. Cl. ................ 128/203.12; 128/203.15; 604/58; 206/538

(58) Field of Classification Search ............. 128/200.24, 128/203.12, 203.15, 203.19, 203.21; 206/461, 206/471, 531, 532, 538, 539, 390, 714; 226/2, 226/3, 6, 62; 604/58
See application file for complete search history.

(56) References Cited

U.S. PATENT DOCUMENTS

| 4,625,902 | A | * | 12/1986 | Billberg | ........................... 226/2 |
| 5,207,217 | A | * | 5/1993 | Cocozza et al. | ......... 128/203.21 |
| 5,497,763 | A | | 3/1996 | Lloyd et al. | |
| 5,794,613 | A | * | 8/1998 | Piskorski | ................. 128/203.12 |
| 7,171,965 | B2 | * | 2/2007 | Young et al. | ............. 128/203.15 |
| 2002/0046750 | A1 | * | 4/2002 | Gonda et al. | ............. 128/200.14 |
| 2003/0079744 | A1 | * | 5/2003 | Bonney et al. | ........... 128/203.12 |

FOREIGN PATENT DOCUMENTS

| EP | 0 467 172 A1 | 1/1992 |
| WO | WO 01/72605 A1 | 10/2001 |
| WO | WO 2004/103446 A1 | 12/2004 |

* cited by examiner

*Primary Examiner* — Justine Yu
*Assistant Examiner* — Valerie L Skorupa
(74) *Attorney, Agent, or Firm* — Sughrue Mion, PLLC

(57) ABSTRACT

A blister pack for an inhaler, the blister pack comprising a blister support (10) with a plurality of blisters (11), each blister (11) being hermetically sealed by a closure layer (20), the blister support (10) being in the form of an elongate strip, the blisters (11) being disposed one after the other along said blister support strip, said blister support (10) including two lateral profiles (15), one on either longitudinal side of said blister support (10), said lateral profiles being formed by alternating depressions (18) and projections (16), each projection including an abutment surface (17) for displacing said blister pack in accurate manner each time said inhaler is actuated, each abutment surface (17) being connected to the adjacent abutment surface (17) via a slide surface (19) formed by each depression.

17 Claims, 2 Drawing Sheets

BLISTER ASSEMBLY FOR INHALATION DEVICE

FIELD OF THE INVENTION

The present invention relates to a blister pack for an inhaler and to an inhaler including such a blister pack.

BACKGROUND

For selectively dispensing doses of fluid, in particular pharmaceutical powder, from an inhaler, it is general practice to use pre-dosed reservoirs known as blisters. Each blister contains one dose of fluid, and one dose of fluid is dispensed each time the inhaler is actuated. The blisters can be formed as blister packs comprising a plurality of blisters, and it has already been proposed to make the blister packs in the form of an elongate strip or a disk. A problem that is posed relates to the displacement of the blister pack in order to bring, on each actuation, a blister into a position to be opened in order to make it possible to dispense the fluid contained therein. The accuracy of the displacement and of the positioning of the blister pack is paramount in providing safe and reliable operation and metered-dose accuracy, in particular at the end of the cycle of the inhaler, i.e. when the last doses are dispensed. In particular in the context of a longitudinal strip or tape, said strip or tape can be made up of one or more layers of relatively deformable material(s). In order to displace said tape, a fairly substantial force is applied thereon, and the deformable character of the tape or of the blister strip means that the tape risks deforming with increasing advance force being exerted thereon. Such deformation can be prejudicial to the accuracy with which the tape is positioned, in particular at the end of the cycle, with it being possible that the above-mentioned drawbacks might appear. A means of solving that problem is to make the blister packs with holes or perforations in the lateral edges of said blister pack, with one or more sprocket wheels coming to penetrate into said perforations so as to cause the blister pack to advance on each actuation, somewhat like a film in a camera. However, that embodiment implies several drawbacks. Firstly, it requires the width of the blister pack to be increased, so as to enable said holes to be made. Unfortunately, the bigger the blister pack, the bigger the inhaler must also be in which said blister pack is mounted, and this can be a drawback in terms of bulkiness, complexity, and thus the cost of manufacturing the assembly. In addition, problems are posed as a result of having to make perforations in a blister pack that might comprise a plurality of layers, some of which are rather strong, e.g. aluminum layers. Thus, when some layers of the multilayer blister packs are relatively strong, the spikes used to make said holes can erode in operation in contact with the strong layers, which can cause said holes to be made less accurately and can thus cause the inhaler to malfunction. Making such lateral holes also requires the use of a complex punching system, and this increases the cost of manufacturing said blister pack.

Document EP-A-0 467 172 discloses a blister strip including lateral profiles on either side of said strip forming a plurality of notches.

Documents WO-A-01/72605 and U.S. Pat. No. 5,497,763 disclose blister packs including a blister support in the form of a strip provided with holes or perforations made in lateral edges. In such an event, one or more sprocket wheels penetrate into said perforations so as to cause the blister pack to advance on each actuation.

OBJECTS OF THE INVENTION

An object of the present invention is to provide an inhaler blister pack that does not have the above-mentioned drawbacks.

More particularly, an object of the present invention is to provide an inhaler blister pack that is small and compact.

Another object of the present invention is to provide an inhaler blister pack that is simple and inexpensive to manufacture and to assemble and that is reliable in use, guaranteeing in particular accurate positioning on each actuation, even when the last doses of the pack are being dispensed.

Another object of the present invention is to provide an inhaler that is simple and inexpensive to manufacture and to assemble and that is reliable in use.

The present invention thus provides an inhaler blister pack as described in claim 1. Advantageous embodiments are described in the dependent claims.

The present invention also provides an inhaler including a blister pack as described above.

Advantageously, the inhaler further includes drive means adapted to co-operate, on each actuation, with a projection of said at least one lateral profile, so as to displace said blister pack in accurate manner.

BRIEF DESCRIPTION OF THE DRAWINGS

Other characteristics and advantages of the present invention appear more clearly from the following detailed description of two embodiments thereof, given by way of non-limiting example, and with reference to the accompanying drawings, and in which.

DETAILED DESCRIPTION OF NON-LIMITING EMBODIMENT

Figure 1:
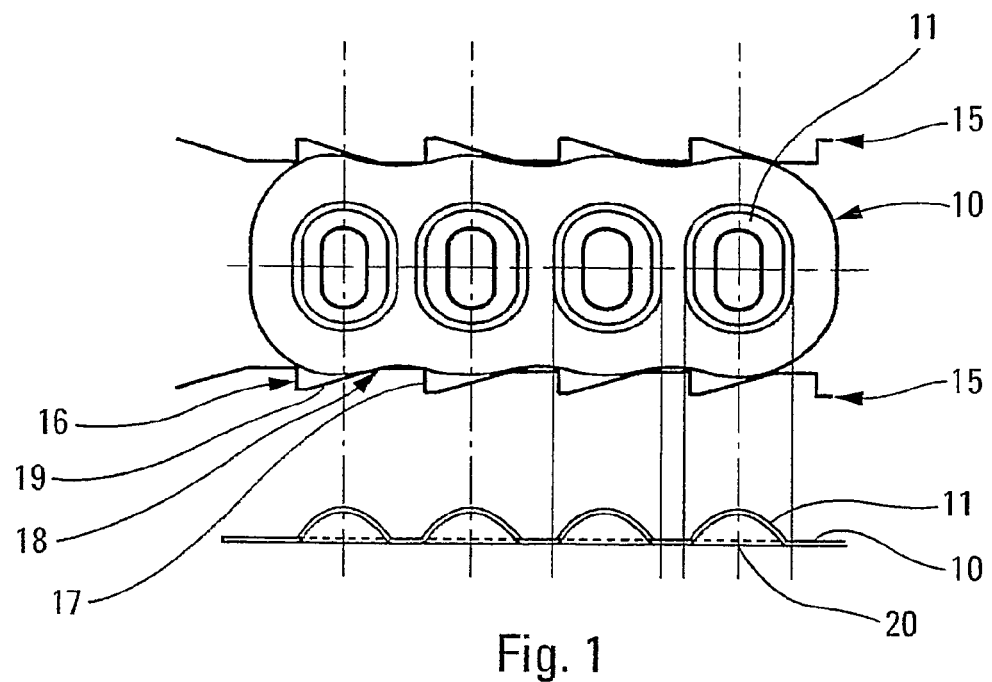
FIG. 1 is a diagrammatic view showing, in its top portion, a blister pack as seen from above, and, in its bottom portion, the same blister pack as seen from the side.

A blister pack for an inhaler includes a blister support 10 provided with a plurality of blisters 11. The blister support can advantageously be made in the form of an elongate strip or tape, as shown in the figures. In this event, the blisters 10 are advantageously disposed one behind the other along said strip, advantageously with a fixed distance between them. Other embodiments can also be envisaged. Each blister 11 of the blister support 10 is closed by a closure layer 20. A single closure layer 20 can advantageously be used to close all of the blisters. In a variant, each blister could have its own respective closure layer. During actuation, the closure layer 20 can be opened by any appropriate means, e.g. by unsticking, cutting, tearing, punching, piercing, or the like. Since opening the blisters does not form part of the present invention, the opening means are not described below. The blister pack is for mounting in an inhaler, and said inhaler can be of any kind, such that it too is not shown or described in greater detail below.

Figure 2:
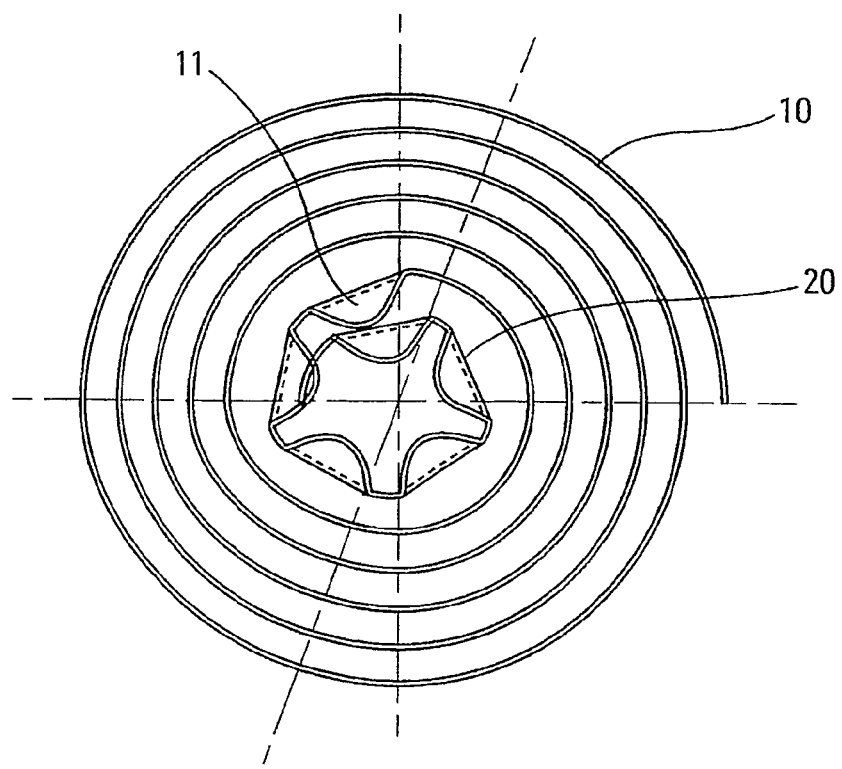
FIG. 2 is a diagrammatic view showing a blister pack in the form of a rolled-up tape, suitable for use in an inhaler.

FIG. 2 shows a particular embodiment in which the blister pack is made in the form of a flexible strip that is suitable for being rolled up so as to be mounted in an inhaler, said strip then being unrolled progressively each time the inhaler is actuated. Other variants can also be envisaged.

In the invention, the blister support 10 includes two lateral profiles 15 extending along said blister support 10. In the context of an elongate strip, the blister support 10 includes two lateral profiles 15, one on either longitudinal side of said strip. As can be seen in the figures, each lateral profile 15 comprises at least one projection 16 for making it possible to displace said blister pack accurately on each actuation of the inhaler in which said blister pack is mounted.

With reference more particularly to FIG. 1, which shows a first advantageous embodiment of the invention, it should be observed that each blister 11 can, on each lateral profile 15, have a projection 16 associated therewith. In the embodiment shown, each blister 11 is therefore associated with two projections 16 disposed on either side of said blister. Each lateral profile 15 is formed by alternating projections 16 and depressions 18, and an abutment surface 17 is provided on each projection 16. The abutment surface 17 is for co-operating with drive means 30 of the inhaler which are described more precisely with reference to FIGS. 4 and 5. Each abutment surface 17 is connected to the directly-adjacent abutment surface 17 via a slide surface 19 enabling the drive means to be displaced in regular manner between two blisters, so as to make it easier to position said drive means in the next projection after each actuation. The abutment surface 17 is advantageously formed by a wall that is approximately transverse relative to the direction along which the blisters 11 extend over said blister support 10.

In the particular embodiment in FIG. 1, in which the blister support 10 is an elongate strip, the abutment surface 17 is approximately perpendicular to the longitudinally-extending edges of said strip. This embodiment makes it possible to position appropriate drive means 30 in each depression 18 in contact with a respective abutment surface 17 of the respective projection 16, so as to cause the blister support 10 to advance without significantly deforming said support. The present invention therefore makes it possible to position better the blister support made in the form of a strip or a tape, by using a profile that reduces deformation, in particular at the end of the advance cycle, while minimizing the width of the tape.

Figure 3:
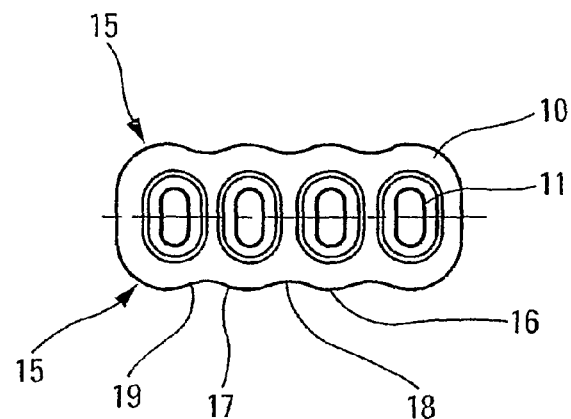
FIG. 3 is a diagrammatic plan view of a variant embodiment of a blister pack of the present invention.
Figures 4, 5:
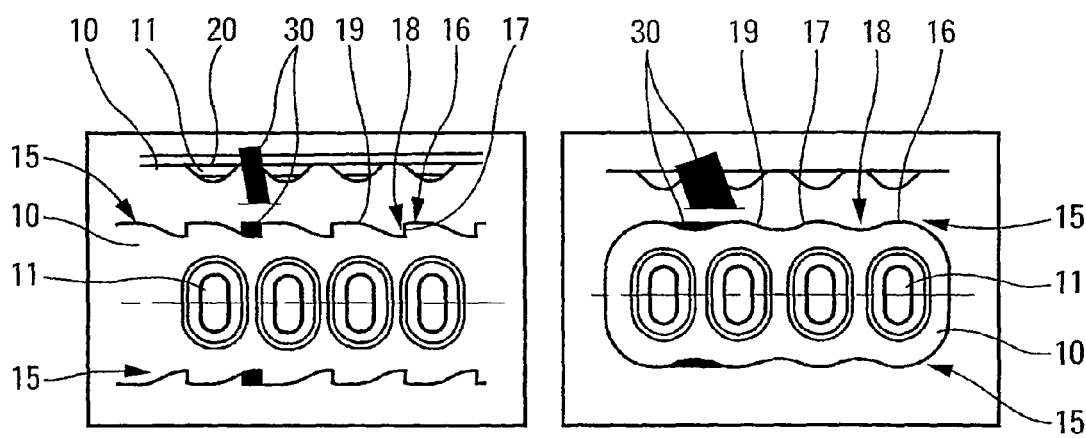
FIGS. 4 and 5 are diagrammatic views showing drive means co-operating with the blister packs of FIGS. 1 and 3 respectively, the top portions of FIGS. 4 and 5 showing the blister packs as seen from the side, whereas the bottom portions of FIGS. 4 and 5 show the blister packs as seen from above.

FIGS. 3 and 5 show a variant embodiment of the invention. This variant embodiment also includes a lateral profile 15 on either side of the tape, said tape being formed by undulations alternating between depressions 18 and projections 16. In this second embodiment, the abutment surface is not as pronounced as in the first embodiment, and, in particular, it is not perpendicular to the lateral edge of the tape, but the presence of the undulating profile likewise makes it possible to advance the blister support without excessively deforming said tape.

The lateral profiles shown in FIGS. 1 and 3 are simple to manufacture by merely cutting out the lateral edges of the tapes. In this way, the width of the blister supports are limited, and this has an impact on the overall size of the blister pack, and consequently also of the inhaler in which it is assembled, in particular if the blister pack contains a large number of doses, as is often the case.

Other modifications and variants can also be envisaged by the person skilled in the art, without going beyond the ambit of the present invention, as defined by the accompanying claims.

The invention claimed is:

1. A blister pack with an inhaler, the blister pack comprising a blister support (10) with a plurality of blisters (11), each blister (11) being hermetically sealed by a closure layer (20), the blister support (10) being in the form of an elongate strip, the blisters (11) being disposed one after the other along said blister support strip, said blister support (10) including two lateral profiles (15), one on either longitudinal side of said blister support (10), said lateral profiles being formed by alternating depressions (18) and projections (16), each projection including an abutment surface (17) for displacing said blister pack in accurate manner each time said inhaler is actuated, wherein each abutment surface (17) is connected to the directly adjacent abutment surface (17) via a slide surface (19) formed by each depression; and each abutment surface and each slide surface is angled relative to each other and relative to a direction along which the blisters extend over the blister support; wherein, upon each actuation, a drive mechanism that is positioned in one of the depressions and in contact with an associated abutment surface of the depression of at least one of the two lateral profiles advances the blister strip by pressing against the associated abutment surface, and moving from said one of the depressions into the next one of the depressions after the drive mechanism advances the blister strip so that the drive mechanism engages each of the depressions sequentially, said slide surface enabling the drive mechanism to be displaced in regular manner between two depressions.

2. A blister pack according to claim 1, in which said abutment surface (17) is formed by a wall (17) that is approximately transverse relative to the direction along which the blisters (11) extend over said blister support (10).

3. A blister pack according to claim 1, in which each abutment surface (17) is approximately perpendicular to the direction along which the blisters extend over the blister support.

4. A blister pack according to claim 1, in which said blister support (10) is an elongate flexible strip that is suitable for being rolled up so as to be mounted in an inhaler.

5. A blister pack according to claim 1, in which each blister (11) is formed by a cavity containing one dose of powder to be dispensed by said inhaler.

6. The blister pack according to claim 1, in which each blister is formed by a rigid cavity containing one dose of powder to be dispensed by said inhaler.

7. The blister pack with an inhaler according to claim 1, wherein the drive mechanism is a finger that projects into each of the depressions in turn.

8. The blister pack with an inhaler according to claim 7, wherein the slide surface is inclined relative to the abutment surface so that the finger slides on the slide surface to contact the adjacent abutment surface.

9. A blister pack with an inhaler, comprising:

a blister support comprising a plurality of blisters, each blister sealed by a closure layer, the blister support having a form of an elongate strip with the blisters disposed one after the other along the blister support strip;

the blister support comprising a first lateral profile on a longitudinal side of the blister support, the first lateral profile comprising alternating depressions and projections, each projection comprising an abutment surface configured to displace the blister pack each time the inhaler is actuated, each abutment surface is connected to a directly adjacent abutment surface via a slide surface formed by each depression; each abutment surface and each slide surface extending at an angle relative to each other and relative to a direction along which the blisters extend over the blister support; and wherein upon each actuation, a drive mechanism that is positioned in one of the depressions and in contact with an associated abutment surface of the depression advances the blister strip by pressing against the associated abutment surface, and moving from said one of the depressions into a directly adjacent one of the depressions after the drive mechanism advances the blister strip so that the drive mechanism engages each of the depressions sequentially, said slide surface enabling the drive mechanism to be displaced between the directly adjacent abutment surfaces for sequential engagement of the depressions.

10. The blister pack according to claim 9, comprising a second lateral profile on a longitudinal side of the blister support opposite the longitudinal side of the blister support for the first lateral profile, the second lateral profile comprising alternating depressions and projections, each projection on the second lateral profile comprising an abutment surface configured to displace the blister pack each time the inhaler is actuated, each abutment surface on the second lateral profile connected to an adjacent abutment surface on the second lateral profile via a slide surface formed by each depression on the second lateral profile; each abutment surface on the second lateral profile and each slide surface on the second lateral profile extending at an angle relative to each other and relative to the direction along which the blisters extend over the blister support.

11. The blister pack according to claim 10, wherein the abutment surface is formed by a wall that is transverse relative to the direction along which the blisters extend over said blister support.

12. The blister pack according to claim 10, wherein each abutment surface is approximately perpendicular to the direction along which the blisters extend over the blister support.

13. The blister pack according to claim 10, wherein the blister support is an elongate flexible strip configured to be rolled up to be mounted in an inhaler.

14. The blister pack according to claim 10, wherein each blister is formed by a cavity containing one dose of powder to be dispensed by the inhaler.

15. The blister pack according to claim 10, wherein each slide surface ramps up to the abutment surface in a direction away from a longitudinal centerline of the blister support.

16. The blister pack according to claim 10, wherein the pattern of projections and depressions form an undulating lateral profile on both longitudinal sides of the blister support.

17. The blister pack according to claim 9, wherein the pattern of projections and depressions form an undulating lateral profile on the longitudinal side of the blister support.

* * * * *